United States Patent
Giesseler et al.

(10) Patent No.: US 12,330,951 B2
(45) Date of Patent: Jun. 17, 2025

(54) SILICA GRANULES FOR THERMAL TREATMENT

(71) Applicant: EVONIK OPERATIONS GMBH, Essen (DE)

(72) Inventors: Mareike Giesseler, Maintal (DE); Rainer Golchert, Dieburg (DE); Nina Mühlig, Schaafheim (DE); Alexander Lygin, Griesheim (DE); Wolfgang Aul, Freigericht (DE); Tobias Renger, Grosskrotzenburg (DE); Christoph Tontrup, Alzenau (DE)

(73) Assignee: Evonik Operations GmbH, Essen (DE)

( * ) Notice: Subject to any disclaimer, the term of this patent is extended or adjusted under 35 U.S.C. 154(b) by 312 days.

(21) Appl. No.: 17/927,040

(22) PCT Filed: May 14, 2021

(86) PCT No.: PCT/EP2021/062797
§ 371 (c)(1),
(2) Date: Nov. 22, 2022

(87) PCT Pub. No.: WO2021/239475
PCT Pub. Date: Dec. 2, 2021

(65) Prior Publication Data
US 2023/0286814 A1    Sep. 14, 2023

(30) Foreign Application Priority Data

May 25, 2020 (EP) .................... 20176242

(51) Int. Cl.
*C01B 33/18* (2006.01)

(52) U.S. Cl.
CPC .......... *C01B 33/18* (2013.01); *C01P 2004/51* (2013.01); *C01P 2004/61* (2013.01); *C01P 2006/10* (2013.01); *C01P 2006/12* (2013.01); *C01P 2006/14* (2013.01); *C01P 2006/82* (2013.01)

(58) Field of Classification Search
None
See application file for complete search history.

(56) References Cited

U.S. PATENT DOCUMENTS

| | | |
|---|---|---|
| 4,042,361 A | 8/1977 | Bihuniak et al. |
| 6,849,242 B1 * | 2/2005 | Koeppler ............... C03C 3/06 65/17.3 |
| 7,541,014 B2 | 6/2009 | Morters et al. |
| 9,567,229 B2 | 2/2017 | Meyer et al. |
| 9,725,326 B2 | 8/2017 | Lindner et al. |
| 10,384,940 B2 | 8/2019 | Katusic et al. |
| 10,752,510 B2 | 8/2020 | Drexel et al. |
| 2004/0253164 A1 | 12/2004 | Mangold et al. |
| 2008/0300356 A1 | 12/2008 | Meyer et al. |
| 2012/0322893 A1 | 12/2012 | Drexel et al. |
| 2016/0082415 A1 | 3/2016 | Drexel et al. |
| 2017/0008772 A1 | 1/2017 | Ueda |
| 2019/0055150 A1 | 2/2019 | Fabian et al. |
| 2019/0062193 A1 | 2/2019 | Otter et al. |
| 2022/0267160 A1 | 8/2022 | Giesseler et al. |
| 2023/0062574 A1 | 3/2023 | Menzel et al. |

FOREIGN PATENT DOCUMENTS

| | | |
|---|---|---|
| EP | 1 717 202 | 11/2006 |
| WO | WO 2007/128349 | 11/2007 |
| WO | WO 2009/007180 | 1/2009 |
| WO | WO 2022/171406 | 8/2022 |

OTHER PUBLICATIONS

International Search Report for corresponding PCT/EP2021/062797, filed May 14, 2021.
Written Opinion of the International Searching Authority for corresponding PCT/EP2021/062797, filed May 14, 2021.
International Preliminary Report on Patentability for corresponding PCT/EP2021/062797, filed May 14, 2021.
European Search Report and Search Opinion for corresponding EP 20176242 , filed May 25, 2020.
U.S. Appl. No. 17/792,471, filed Jul. 13, 2022, Menzel.
U.S. Appl. No. 17/667,727, filed Feb. 9, 2022, US-2022/0267160, Aug. 25, 2022, Giesseler.

* cited by examiner

Primary Examiner — Michael Forrest
(74) Attorney, Agent, or Firm — Law Office of: Michael A. Sanzo, LLC

(57) ABSTRACT

The invention provides fumed silica granules having a BET surface area of 20 m²/g to 500 m²/g; a number average particle size $d_{50}$ of 350 μm to 2000 μm; a span $(d_{90}-d_{10})/d_{50}$ of particle size distribution of 0.8-3.0; a bulk density of more than 0.35 g/mL; a pore volume for pores >4 nm of not more than 1.5 cm³/g, process for its preparation and use thereof as a catalyst carrier, a carrier for liquid substances, in cosmetic applications, for thermal insulation, as pharmaceutical excipient, in producing thermally treated silica granules, as an abrasive, as a component of a silicone rubber.

20 Claims, No Drawings

SILICA GRANULES FOR THERMAL TREATMENT

CROSS REFERENCE TO RELATED APPLICATIONS

The present application is US national stage of international application PCT/EP2021/062797, which had an international filing date of May 14, 2021 and which was published on Dec. 2, 2021. The application claims priority to EP 20176242.4, filed on May 25, 2020. The content of these prior applications is hereby incorporated by reference in its entirety.

The invention relates to fumed silica granules, preparation and use thereof for producing thermally treated silica granules.

Granules based on fumed silica can be used for a variety of different applications, e.g. as catalyst carriers, carriers for liquid substances, in cosmetic applications, for thermal insulation, as pharmaceutical excipients etc.

For some applications, such as for producing of catalyst carriers or abrasive materials, silica granules need to undergo a thermal treatment step. During this step, which is typically carried out at temperatures of above 300-500° C., all the volatile residues are eliminated, and the number of free silanol groups on the surface of silica and the overall porosity is substantially reduced. Such thermally treated silica granules usually possess a higher bulk density, than their precursors. It is common that an often-undesired agglomeration to larger silica fragments and clogging takes place during the thermal treatment step.

Numerous methods for preparing fumed silica granules from fumed silica powder dioxide, which can be used as precursors for subsequent thermal treatment, are known. The preparation usually includes an agglomeration of the fumed silica particles. This can be done by means of a wet granulation. In the wet granulation, an aqueous colloidal fumed silica dispersion is usually prepared under constant mixing. The solvents are then gradually removed to leave a dry residue, which can be further crashed and classified.

US 20170008772 A1 describes preparation of a synthetic amorphous silica powder by a process comprising the following steps: (a) forming and subsequent drying a fumed silica slurry, for example in a rotary kiln to obtain silica powder; (b) primary firing of the obtained silica powder at 900-1200° C.; (c) pulverization and a secondary firing at 1100-1400° C.; (d) pulverization and washing; (e) filtration to obtain the target sintered silica powder. The non-sintered silica granules obtained in step (a) of this process by evaporation of water from a silica slurry are not mechanically compacted and thus possess relatively high porosity and low bulk density. The sintered silica particles obtained after step (b) of the process, on the contrary, possess almost no porosity and a very low BET surface area.

U.S. Pat. No. 4,042,361 discloses a process for preparing silica granules, in which pyrogenic silicon dioxide is used. This is incorporated into water to form a dispersion, then the water is evaporated under heating, the residue is crushed into pieces varying from about a millimetre to several centimetres in size, which are further calcined at 1150° C. to 1500° C.

One special type of wet granulation processes is based on a spray-drying of the silica dispersion to obtain spherical granules with a narrow particle size distribution.

EP 1717202 A1 discloses preparation of a silica-based sintered material, with a mean particle diameter of 10-120 µm involving a step of spray-drying of a dispersion comprising fumed silica and subsequent thermal treatment of silica granules.

It is also possible to obtain silica granules by dry compacting silicon dioxide. The compacting, of dry pyrogenic silicon dioxide is difficult because pyrogenic silicon dioxide is very dry, and no capillary forces can bring about the particle binding. Pyrogenic silicon dioxides feature extreme fineness, a low bulk density, high surface area, very high purity, a substantially spherical primary particle shape and the absence of pores. The pyrogenic silicon dioxide frequently has a high surface charge, which complicates the agglomeration because of electrostatic interactions.

WO 2009007180 A1 discloses a process for producing silica granule with a BET surface area of <1 m² and a medium particle diameter of 10-140 µm, which can be produced by (a) compacting pyrogenic silicon dioxide powder to slugs; (b) crushing these slugs, and removing the slug fragments of <100 µm and >800 µm; (c) treating the resulting slug fragments with a tamped density of 300-600 g/L at 600-1100° C. in an atmosphere suitable for removing hydroxyl groups and (d) sintering at 1200-1400° C.

US20160082415A1 relates to providing functionalized silica carrier materials with improved desorption characteristics, e.g. for sorption of enzymes. US20160082415A1 disclosed a process for producing such functionalized granular silicas comprising shaping precipitated or fumed silicas by dry compaction to give slugs, screen granulation or screening thereof at a screen size of 3000 µm, screening off the fines followed by reacting the obtained granules with a surface modifier. Only the specific examples of precipitated silica granules are given in this patent application.

US20190053150A1 and US20190062193A1 both disclose processes for preparation of fumed silica granules with a pore volume of 0.1 to 2.5 mL/g, a bulk density of 0.5-1.2 g/cm³, a mean particle size $d_{50}$ in the range 150-300 µm by spray drying the aqueous dispersion and subsequent melting of the silica granules.

Selection of a suitable silica precursor for preparing thermally treated silica articles, is of paramount importance. Many types of silica granules known from the prior art are not optimal for carrying out such thermal treatment processes, resulting in lower performance, clogging, and inferior product properties of the thermally treated silica products.

The object of the present invention is that of providing a granular silica-based material optimized for producing thermally treated silica granules with an increased bulk density, especially by a continuous process.

Such silica-based granular material should be suitable for continuous thermal treatment in a rotary kiln or similar devices, with a high throughput and without clogging.

Fumed Silica Granules

The invention provides fumed silica granules having:
- a BET surface area of 20 m²/g-500 m²/g;
- a number average particle size $d_{50}$ of 350 µm to 2000 µm, as determined by laser diffraction method;
- a span $(d_{90}-d_{10})/d_{50}$ of particle size distribution of 0.8-3.0, as determined by laser diffraction method;
- a bulk density of more than 0.35 g/mL, as determined by mercury intrusion method; a pore volume for pores >4 nm of not more than 1.5 cm³/g, as determined by mercury intrusion method.

In the context of the present invention, the terms "granular material", "granulate" and "granules" are used as alternatives and are understood to mean a grainy, readily pourable, free-flowing particulate solid material. The granules of the present invention may be in the form of grainy particles with a spherical or any other shape, like pellets, rings etc. or irregularly formed fragments of any crushed molded body, e.g. with a statistical particle size distribution.

The granules of the invention are made of fumed silica. Fumed silicas can be prepared by means of flame hydrolysis or flame oxidation. This involves oxidizing or hydrolyzing of hydrolysable or oxidizable starting materials, generally in a hydrogen/oxygen flame. Starting materials used for pyrogenic methods include organic and inorganic substances. Silicon tetrachloride is particularly suitable. The hydrophilic silica thus obtained is amorphous. Fumed silicas are generally in aggregated form. "Aggregated" is understood to mean that what are called primary particles, which are formed at first in the genesis, become firmly bonded to one another later in the reaction to form a three-dimensional network. The primary particles are substantially free of pores and have free hydroxyl groups on their surface.

The granules according to the invention consist essentially of fumed silica, i.e. contain at least 85%, preferably at least 90%, more preferably 95%-100% by weight of fumed silica. Apart from fumed silica, the granules can contain water and some minor impurities.

The sum of the metal impurities in the inventive granules is preferably less than 500 ppm, more preferably less than 200 ppm, more preferably less than 100 ppm, more preferably less than 50 ppm.

Minor impurities may comprise Ca, Cu, K, Li, Mg, Mn, Na, Ti, V, Zr, Al, B, Cr, Ni, P. To determine the metal content, the silica granules are dissolved in a solution containing hydrofluoric acid. The silicon tetrafluoride which forms evaporates, and the remaining residue is analysed by means of inductively coupled plasma mass spectrometry (ICP-MS).

Particle size distribution of the inventive granules may have a substantial impact on applicability of such silica granules for processes involving thermal treatment.

The granules according to the present invention have a number average particle size $d_{50}$ of 350 μm to 2000 μm, preferably from 350 μm to 1800 μm, more preferably from 350 μm to 1600 μm, more preferably from 400 μm to 1400 μm, more preferably from 400 μm to 1200 μm, more preferably from 500 μm to 1150 μm, more preferably from 550 μm to 1100 μm, even more preferably from 600 μm to 1050 μm and most preferably from 700 μm to 1000 μm. A number average particle size of the granules can be determined according to ISO 13320:2009 by laser diffraction particle size analysis. The resulting measured particle size distribution is used to define the average value $d_{50}$, which reflects the particle size not exceeded by 50% of all particles, as the number average particle size.

The granules according to the present invention preferably have a $d_{10}$ value of from 100 μm to 1000 μm, more preferably from 120 μm to 900 μm, more preferably from 150 μm to 850 μm, more preferably from 200 μm to 800 μm, more preferably from 250 am to 750 μm, more preferably from 300 μm to 700 μm. The preferred $d_{50}$ value is 800 am to 2500 μm, more preferably from 900 μm to 2000 μm, more preferably from 950 am to 1900 μm, more preferably from 1000 μm to 1800 μm. The $d_{10}$ and $d_{50}$ values can be determined according to ISO 13320:2009 by laser diffraction particle size analysis. The resulting measured particle size distribution is used to define the values $d_{10}$ and $d_{90}$, which reflects the particle size not exceeded by 10% or 90% of all particles, respectively.

The granules of the invention preferably have a particle size of not more than 2000 μm, more preferably of not more than 1700 μm, more preferably of not more than 1500 μm, more preferably of not more than 1300 μm. The absence of the particles with a particle size of above the specified range can be achieved for example by sieving of the granules through an appropriate sieve.

The ratio of the particles with a particle size of not more than 100 am in the inventive granules is preferably less than 30% by weight, more preferably less than 20% by weight, more preferably less than 15% by weight, more preferably less than 10% by weight. This ratio can be calculated from the results of particle size analysis by laser diffraction method.

The granules of the invention have a relatively narrow particle size distribution, which can be characterized by a value of span $(d_{50}-d_{10})/d_{50}$ of particle size distribution of 0.8-3.0, preferably 0.9-2.0, more preferably 1.0-1.8, more preferably 1.1-1.7, more preferably 1.2-1.6. It was found that granules with such a narrow particle size distribution can be particularly suitable for carrying out thermal treatment in a continuous way. A narrow particle size distribution of the inventive silica granules results from a presence of relatively low ratios of both fines and the larger silica granules. Silica fines may lead to clogging during the continuous thermal treating process. Larger silica granules may be mechanically unstable during the continuous thermal treatment process, e.g. in a rotary kiln, and disaggregate to form fines.

The term "pore volume of pores >4 nm" relates to a cumulative pore volume of pores >4 nm, which can be determined by the mercury intrusion method according to DIN ISO 15901-1. The principle of this method firstly described by H. L Ritter and L. C Drake in Ind. Eng. Chem. Anal. Ed. 17 (1945) pp. 782-786 and pp 787-791, is based on measurement of the volume of mercury pressed into a porous solid body as a function of the pressure applied. Only the pores into which mercury can penetrate, i.e. generally the pores with a pore diameter of >4 nm, at the maximal pressure applied, e.g. 417 MPa, are detected. Liquid mercury, not wetting the surface of a probe porous solid body, penetrates the pores only under pressure. The pressure to be applied is inversely proportional to the open width of the pore openings, In the case of cylindrical pores, the relationship between pore radius $r_p$ and pressure p is given by the Washburn equation:

$$r_p = -(2 \times \sigma/p) \times \cos \theta$$

wherein:
$r_p$ is pore radius
p is pressure
σ is surface tension of mercury (0.48 N/m)
θ is contact angle of mercury (140° C.)

The pore volume of pores >4 nm corresponds to the cumulative pore volume of all pores determinable by mercury intrusion method according to DIN ISO 15901-1 up to the determination limit at maximum pressure of 417 MPa.

The pore volume of pores >4 nm of the granules of the present invention determined by mercury intrusion method according to DIN ISO 15901-1 is not more than 1.5 cm$^3$/g, preferably 0.1 cm$^3$/g-1.5 cm$^3$/g, more preferably 0.2 cm$^3$/g-1.45 cm$^3$/g, more preferably 0.3 cm$^3$/g-1.4 cm$^3$/g more preferably 0.5 cm$^3$/g-1.3 cm$^3$/g, more preferably 0.6 cm$^3$/g-1.2 cm$^3$/g, more preferably 0.7 cm$^3$/g-1.1 cm$^3$/g, more preferably 0.8 cm$^3$/g-1.0 cm$^3$/g.

The term "pore volume of pores <4 μm" relates to the cumulative pore volume of pores <4 μm, which can be determined by mercury intrusion method according to DIN ISO 15901-1 and corresponds to the cumulative pore volume of all pores <4 μm determinable by this method.

The pore volume of pores <4 µm of the granules of the present invention determined by mercury intrusion method according to DIN ISO 15901-1 is preferably less than 1.4 cm$^3$/g, more preferably 0.05 cm$^3$/g-1.4 cm$^3$/g, more preferably 0.1 cm$^3$/g-1.3 cm$^3$/g, more preferably 0.2 cm$^3$/g-1.25 cm$^3$/g, more preferably 0.3 cm$^3$/g-1.2 cm$^3$/g, more preferably 0.4 cm$^3$/g-1.2 cm$^3$/g, more preferably 0.4 cm$^3$/g-1.1 cm$^3$/g, more preferably 0.4 cm$^3$/g-1.0 cm$^3$/g, more preferably 0.4 cm$^3$/g-0.9 cm$^3$/g, more preferably 0.5 cm$^3$/g-0.9 cm$^3$/g, more preferably 0.6 cm$^3$/g-0.9 cm$^3$/g.

The percent ratio of a pore volume for pores <4 µm to a cumulative pore volume of pores >4 µm of the inventive granules, both pore volumes determined by mercury intrusion method according to DIN ISO 15901-1, is preferably greater than 35%, more preferably greater than 40%, more preferably greater than 50%, more preferably 55%-95%, more preferably 60%-90%, more preferably 65%-85%, more preferably 70%-80%. The percent ratio of a pore volume for pores <4 am to a cumulative pore volume of pores >4 nm can be found by dividing of the former by the latter pore volume and multiplying the result with 100%.

The porosity of the granules determined by mercury intrusion method according to DIN ISO 15901-1 is preferably less than 77%, more preferably 10%-75%, more preferably 20%-70%, more preferably 30%-75%, more preferably 40%-72%, more preferably 50%-70%, more preferably 52%-67%, more preferably 55%-65%.

The granules according to the invention are characterized by a limited porosity and pore volume determined by mercury intrusion method, when compared to similar silica materials known from the prior art. Without wishing to be bound by any theory, it is believed that such reduced porosity correlates with the lower rate of evaporation of water and removal of free silanol groups from the silica surface under thermal treatment. Consequently, if the porosity and pore volume are too high, when fast sintering of the thermally treated silica granules can occur, leading to clogging and reducing the performance during the sintering process.

The granules of the invention have a BET surface area of 20 m$^2$/g to 500 m$^2$/g, preferably of 30 m$^2$/g to 450 m$^2$/g, more preferably of 40 m$^2$/g to 400 m$^2$/g, more preferably of 50 m$^2$/g to 380 m$^2$/g, more preferably of 60 m$^2$/g to 350 m$^2$/g, more preferably of 70 m$^2$/g to 320 m$^2$/g, more preferably of 80 m$^2$/g to 320 m$^2$/g, more preferably of 80 m$^2$/g to 220 m$^2$/g The specific surface area, also referred to simply as BET surface area, can be determined according to DIN 9277:2014 by nitrogen adsorption in accordance with the Brunauer-Emmett-Teller method.

The granules according to the invention preferably have a tamped density of more than 200 g/L, more preferably of 200 g/L to 1000 g/L, more preferably of 230 g/L to 800 g/L, more preferably of 250 g/L to 700 g/L, more preferably of 280 g/L to 650 g/L, more preferably of 300 g/L to 600 g/L, more preferably of 320 g/L to 550 g/L.

Tamped densities of various pulverulent or coarse-grain granular materials can be determined according to DIN ISO 787-11:1995 "General methods of test for pigments and extenders—Part 11: Determination of tamped volume and apparent density after tamping". This involves measuring the apparent density of a bed after agitation and tamping.

Bulk density of the granules according to the invention determined by mercury intrusion method is more than 0.35 g/mL, more preferably 0.35 g/mL-1.20 g/mL, more preferably 0.40 g/mL-1.1 g/mL, more preferably 0.45 g/mL-1.0 g/mL, more preferably 0.47 g/mL-0.95 g/mL, more preferably 0.50 g/mL-0.90 g/mL, more preferably 0.55 g/mL-0.85 g/mL, more preferably 0.60 g/mL-0.80 g/mL. Bulk density of the inventive granules can be determined by mercury intrusion method according to DIN ISO 15901-1 at the minimal mercury pressure applied in this method, for example at pressure <0.01 MPa, e.g. 0.0031 MPa.

Bulk density determined by mercury intrusion method is believed to be a more appropriate value for defining material density of the granular material compared with e.g. tamped density of the same material. Thus, the bulk density determined by mercury intrusion method excludes the large spaces between particles, where mercury can penetrate at the minimal applied pressure, whereas the tamped density defines the density of the material including all the interparticular space.

Relatively high bulk density of the inventive granules correlates with their increased mechanical strength, which is very beneficial for further handling or further treatment, especially thermal treatment of such silica materials. If such a thermal treatment is carried out in a continuous way, e.g. in a rotary kiln or similar devices, the increased mechanical strength of silica granules supresses the formation of unwanted fines and clogging during this process.

Process for Preparing the Granules

The invention further provides a process for preparing the inventive granules comprising the following steps:

a) compaction of fumed silica with a water content of 0.1%-10% by weight to obtain compacted silica fragments with a tamped density of at least 200 g/L;

b) crushing of the compacted silica fragments obtained is step a) under isolation of the crushed fragments with a size of not more than 2000 µm using a sieve with a maximal mesh size of 1000 µm-2000 µm;

c) separation of fine particles from the crushed fragments with a size of not more than 2000 µm obtained in step b) using a sieve with a maximal mesh size of 200 µm-600 µm to obtain the granules;

d) optional employing in step a) the fine particles with a particle size of not more than 600 µm separated in step c).

Process of the invention preferably comprises all steps a) to d). In this case, silica fines with a particle size of not more than 600 µm, more preferably of not more than 500 µm, more preferably of not more than 400 µm separated in step c) can be mixed with fresh fumed silica and used again in step a) of the process. This reduces the amount of wasted silica material and increases the overall yield of the process.

Steps a)-d) of the process according to the invention are preferably carried out sequentially, i.e. step a) is followed by step b), then c) and finally step d).

Process of the invention can be carried out batchwise, semi-continuously, or preferably continuously.

In step a) of the inventive process, a fumed silica with a number average particles size $d_{50}$ of not more than 600 µm can be employed, preferably 5 µm-500 µm, more preferably 10 µm-400 µm, more preferably 15 µm-300 µm, more preferably 20 µm-200 µm. The number average particle size $d_{50}$ of the fumed silica can be determined according to ISO 13320:2009 by laser diffraction particle size analysis.

In step a) of the process, fumed silica with a water content of 0.1%-10% by weight, preferably 0.3%-8.0% by weight, more preferably 0.5%-5.0% by weight, more preferably 1.0%-3.0% by weight, is employed as a starting material for producing silica granules. It was surprisingly found that this selected water content of fumed silica allows producing silica granules with improved mechanical properties and higher production rate. To achieve the required water content of the fumed silica, water can be added before or during the step a) of the inventive process using any suitable techniques or device. Water can e.g. be sprayed onto the fumed silica to achieve its homogeneous distribution.

Fumed silica employed in step a) of the inventive process can have tamped density of 15 g/L to 190 g/L, preferably 20 g/L to 150 g/L, more preferably 30 g/L to 100 g/L, more preferably 40 g/L to 80 g/L.

Fumed silica is compacted in step a) to obtain compacted silica fragments with a tamped density of at least 200 g/L, preferably of 200 g/L to 1000 g/L, more preferably of 230 g/L to 800 g/L, more preferably of 250 g/L to 700 g/L, more preferably of 280 g/L to 650 g/L, more preferably of 300 g/L to 600 g/L, more preferably of 320 g/L to 550 g/L. Tamped density of fumed silica and of compacted silica fragments can be determined according to DIN ISO 787-11:1995.

The relatively high tamped density of the compacted fragments obtained in step a) of the inventive process lead to a higher mechanical strength thereof, less fines formation and eventually a higher sintering performance of the silica granules in the continuous thermal treatment of such silica granules.

Compaction in step a) of the process is understood to mean mechanical compression, preferably without addition of any binder. The compaction should ensure uniform pressing of the fumed silica powder in order to obtain the compacted silica fragments with a substantially equal tamped density.

Step a) of the inventive process can be realized by any suitable device. e.g. by compaction of the fumed silica in a roller compactor, resulting in compacted silica fragments in the form of strip-like intermediates. The properties of such compacted silica fragments can be influenced by the process parameters, such as the selected process control mode, the compacting force, the width of the gap between the two rollers and the pressure hold time which is established by the appropriate change in the rotational speeds of the pressing rollers.

The compaction to compacted silica fragments can be achieved by means of two rollers, of which one or else both may simultaneously have a venting function.

Preferably, two compacting rollers can be used, which may be smooth or profiled. The profile may be present either only on one compacting roller or on both compacting rollers. The profile may consist of axially parallel corrugations or of any arrangement of recesses (depressions) in any configuration. In a further embodiment of the invention, at least one of the rollers may be a vacuum roller compactor.

For the compaction in step a) of the inventive process, a suitable process is especially one in which the fumed silica to be compacted is compacted by means of two compression rollers. One of such rollers can be arranged so as to be driveable with rotation. Alternatively, both compacting rollers can also be non-driveable. The specific pressures applied between two compacting rollers can be from 5 kN/cm to 50 kN/cm, preferably more than 12 kN/cm, more preferably more than 12 kN/cm and less than 30 kN/cm, more preferably more than 12 kN/cm and less than 18 kN/cm.

After compaction in step a) of the process, the obtained compacted silica fragments are crushed in step b) using a sieve with a maximal mesh size of 1000 µm-2000 µm, preferably 1000-1500 µm under isolation of the crushed fragments with a particle size of not more than 2000 µm, preferably not more than 1500 µm. Step b) of the process can be conducted using any suitable device having a sieve and capable of crushing the silica fragments, e.g. in a screen granulator.

For the crushing of the compacted silica fragments in step b) of the process, an apparatus with two contra rotatory rollers with a defined gap or a spiked roller may be used.

In step c) of the inventive process, the in step b) isolated crushed fragments with a particle size of <2000 µm are further subjected to separation of fine particles having a particle size of not more than 600 µm, preferably not more than 550 µm, more preferably not more than 500 µm, using a sieve with a mesh size of 200 µm-600 am, preferably 250 µm-600 µm, more preferably 300 µm-600 µm, more preferably 350 µm-600 µm, more preferably 400 µm-600 µm.

A relatively small difference between the mesh sizes applied in steps b) and c) of the inventive process lead to a narrow particle size distribution of the obtained silica granules, which is particularly beneficial for enhancing sintering performance of the continuous sintering process using such silica granules.

Step c) of the inventive process can be carried out by means of any suitable device, having a sieve e.g. a sifter, a screen or a classifier. The sifters used may be crossflow sifters, counter current deflection sifters, etc. The classifier used may be a cyclone.

The particles having a particle size of not more than 600 µm, separated in step c) of the inventive process are optionally employed in step a) of the process.

The process according to the invention can further comprise optional purification step e). In step e) of the process, the granules obtained in step c) of the process are exposed at temperature of 400° C. to 1100° C., preferably 600° C. to 900° C., to an atmosphere which comprises one or more reactive compounds which are suitable for removing hydroxyl groups and impurities. These may preferably be chlorine ($C_2$), hydrochloric acid (HCl), sulphur halides, e.g. $SCl_2$, $S_2Cl_2$, $SC_4$, and/or sulphur oxide halides, e.g. $SOCl_2$, $SO_2Cl_2$, hydrogen, or mixtures thereof. More preferably, chlorine, hydrochloric acid, disulphur dichloride or thionyl chloride may be used. Usually, the reactive compounds are used as gas mixtures with air, oxygen, helium, nitrogen, argon and/or carbon dioxide. The proportion of the reactive compounds in such gas mixtures can be 0.5% to 20% by volume.

Use of the Granules

The granules according to the invention can be used for a variety of different applications, e.g. as a catalyst carrier, a carrier for liquid substances, in cosmetic applications, for thermal insulation, as a pharmaceutical excipient, as an abrasive, as a component of a silicone rubber etc.

The inventive granules are particularly suitable for producing thermally treated silica granules, especially in a continuous process.

Such thermal treatment can be conducted in any suitable apparatus, e.g. in a suitable rotary kiln. In order to produce thermally treated granules of particularly high purity, especially, low metal content, potential contamination during the thermal treatment step should be avoided. For this purpose, the material of thermal treatment device should be selected accordingly.

Thermal treatment is preferably conducted at the temperature of at least 300° C., more preferably at least 500° C., more preferably at least 700° C., more preferably at least 900° C., more preferably at least 1000° C., more preferably at least 1100° C., more preferably at least 1200° C.

In some cases, it may be beneficial to conduct the thermal treatment of the inventive granules in several steps, e.g. in two, three or more steps, with a different, sequentially increasing temperatures individually adjusted in each thermal treatment step. It was surprisingly found that the overall throughput of such thermal treatment process may be increased, and no unwanted blocking of the thermal treatment devices occur. Preferably, thermal treatment of the inventive granules is conducted at the first thermal treatment temperature and then at least at the second thermal treatment temperature, wherein the second thermal treatment temperature is at least 10° C., preferably at least 20° C., more preferably at least 30° C., more preferably at least 40° C., more preferably at least 50° C. higher than the first thermal treatment temperature.

Particularly preferably, the granules according to the invention can be used as a precursor for producing thermally treated high density silica granules, e.g. in the form of a catalyst carrier, a carrier for liquid substances; as a component of a cosmetic formulation, of a thermal insulation composition, as a pharmaceutical excipient, as an abrasive, as a component of a silicone rubber etc.

EXAMPLES

Particles size of the particles ($d_{10}$, $d_{50}$, $d_{50}$) was measured using a laser diffraction analyzer Beckman Coulter LS in a dry state.

Bulk density, porosity and the cumulative pore volume for pores larger than 4 nm were determined by the mercury intrusion method according to DIN ISO 15901-1 using AutoPore V 9600 device (Micomeritics). Only the pore volume of pores into which mercury can penetrate, i.e. the pores with a pore diameter of >4 nm, at the maximal pressure applied (417 MPa) was detected.

Specific BET surface area [$m^2$/g] was determined according to DIN 9277:2014 by nitrogen adsorption in accordance with the Brunauer-Emmett-Teller method.

Preparation of Silica Granules

Example 1 (According to the Invention)

Fumed silica powder AEROSIL©90 (BET=90 $m^2$/g, manufacturer: Evonik Resource Efficiency GmbH) is placed in a storage tank and treated with the demineralized water in a mixing unit (target value 1.5 wt % $H_2O$). In this unit, the fines resulting from screening in one of the following process steps are then added and homogenized. From there, the material flows unfed, i.e. only due to its mass, into a hopper in which a stuffing screw rotates. The hopper is subjected to negative pressure from outside. Its walls consist of a cloth-covered sintered metal. While the material is vented by the vacuum, the stuffing screw transports the fumed silica powder to the rolls. Between the rolls, which have a corrugated profile (6 mm), the material is compressed with a specific pressure of more than 12 kN/cm and less than 18 kN/cm. Due to the corrugated profile, "rods" of compressed, compacted fumed silica are formed. These rods are then crushed in a screen granulator. The mesh size in the screen granulator is 1250 μm. The mesh size in the screen granulator limits the upper grain size. The lower size is defined in the subsequent screening.

In a screen with ultrasonic cleaning, the material broken up in the screen granulator is screened and the undersize is separated. The mesh size is 500 μm. The fines are returned to the storage container by a vacuum cycle conveyor.

Comparative Example 1

Conducted as example 1 but using a sieve with a mesh size of 100 μm instead of a sieve with a 500 μm mesh size used in example 1, in a subsequent screening.

Comparative Example 2

Silica granules were prepared from an aqueous dispersion containing 20 wt % AEROSIL© 90 by spray drying techniques (atomization by nozzle, pressure of dispersion: 8 bar) at an inlet temperature of 350° C. and outlet temperature of the spray-drier of 100° C.). Drying took place in a counter-flow mode. The product was post treated in a fluidized bed to further increase agglomerate size. The finished product was separated by a filter.

Silica granules of example 1 and comparative examples 1 and 2 have the physico-chemical properties summarized in Table 1.

Thermal Treatment of Silica Granules

Silica granules of example 1 and comparative examples 1 and 2 were thermally treated continuously in a rotary kiln of ca. 140 mm diameter and 2 m length under identical conditions (maximal temperature=1350° C.). The feed rate of silica granules was continuously increased in each case until the first signs of overload and congestion were apparent. Thus, the maximal sintering performance [in kg/h] was determined and compared for different granules (Table 1).

The silica granules prepared in example 1 turned out to have a much higher maximal throughput rate without any congestion, than the silicas from comparative examples 1 and 2 (Table 1).

Granules of all three types have similar BET surface areas. Due to their preparation, the granules of example 1 have higher average particle size, higher bulk density, lower porosity and pore volume for pores >4 nm, than other granules (Table 1). Silica granules from comparative example 2 have a much higher flowability (data not shown in Table 1) and a narrower particle size distribution than the granules from example 1. Nevertheless, silica granules from example 1 achieve a higher maximal sintering performance, which cannot be explained purely by a particle form or size, but by a particularly suitable combination of relatively large average particle size, relatively low porosity and high bulk density of such granules.

TABLE 1

Properties of silica granules

| Example | $d_{50}$ [μm] | Ratio of particles < 100 μm, wt. % | ($d_{90}$-$d_{10}$)/$d_{50}$ | BET [$m^2$/g] | Bulk density by Hg-intrusion [g/mL] | pore volume > 4 nm by Hg-intrusion [mL/g] | Porosity by Hg-intrusion [%] | Maximal sintering performance [kg/h] |
|---|---|---|---|---|---|---|---|---|
| Example 1 | 920 | 5 | 1.40 | 93 | 0.665 | 0.88 | 58.4 | 6 |
| Comparative Example 1 | 252 | 30 | 4.15 | 92 | 0.469 | 1.67 | 78.0 | 2 |

TABLE 1-continued

Properties of silica granules

| Example | $d_{50}$ [μm] | Ratio of particles < 100 μm, wt. % | $(d_{90}-d_{10})/d_{50}$ | BET [m²/g] | Bulk density by Hg-intrusion [g/mL] | pore volume > 4 nm by Hg-intrusion [mL/g] | Porosity by Hg-intrusion [%] | Maximal sintering performance [kg/h] |
|---|---|---|---|---|---|---|---|---|
| Comparative Example 2 | 148 | 27 | 1.19 | 83 | 0.335 | 2.38 | 79.4 | 0.5 |

The invention claimed is:

1. Fumed silica granules comprising:
   a BET surface area of 20 m²/g to 500 m²/g;
   a number average particle size $d_{50}$ of 350 μm to 2000 μm, as determined by laser diffraction;
   a span $(d_{90}-d_{10})/d_{50}$ of particle size distribution of 0.8-3.0, as determined by laser diffraction;
   a bulk density of more than 0.35 g/mL, as determined by mercury intrusion;
   a pore volume for pores >4 nm of not more than 1.5 cm³/g, as determined by mercury intrusion.

2. The fumed silica granules of claim 1, wherein the $d_{10}$ of the granules is from 100 μm to 1000 μm, as determined by laser diffraction.

3. The fumed silica granules of claim 1, wherein the percentage of particles with a particle size of not more than 100 μm is less than 20% by weight of the granules.

4. The fumed silica granules of claim 1, wherein the span $(d_{90}-d_{10})/d_{50}$ of particle size distribution of the granules is 0.9-2.0.

5. The fumed silica granules of claim 1, wherein the tamped density of the granules is 300 g/L-600 g/L.

6. The fumed silica granules of claim 1, wherein the granules have a porosity of less than 77%, as determined by mercury intrusion.

7. The fumed silica granules of claim 2, wherein the particles with a particle size of not more than 100 μm is less than 20% by weight of the granules.

8. The fumed silica granules of claim 7, wherein the span $(d_{90}-d_{10})/d_{50}$ of particle size distribution of the granules is 0.9-2.0.

9. The fumed silica granules of claim 8, wherein the tamped density of the granules is 300 g/L-600 g/L.

10. The fumed silica granules of claim 9, wherein the granules have a porosity of less than 77%, as determined by mercury intrusion.

11. A process for preparing the fumed silica granules of claim 1, comprising the following steps:
   a) compacting fumed silica with a water content of 0.1%-10% by weight to obtain compacted silica fragments with a tamped density of at least 200 g/L;
   b) crushing the compacted silica fragments obtained is step a) and isolating crushed fragments with a size of not more than 2000 μm using a sieve with a mesh size of 1000 μm-2000 μm;
   c) separating fine particles from the crushed fragments with a size of not more than 2000 μm obtained in step b) using a sieve with a mesh size of 200 μm-600 μm;
   d) optionally repeating step a) with the sieved fine particles obtained in step c).

12. The process of claim 11, wherein the process is carried out continuously.

13. The process of claim 11, wherein, in step a), a fumed silica with a water content of 0.5%-5.0% by weight is used.

14. The process of claim 11, wherein the mesh size of the sieve used in step b) of the process is 1000 μm-1500 μm.

15. The process of claim 11, wherein the mesh size of the sieve used in step c) of the process is 400 μm-600 μm.

16. The process of claim 11, further comprising step e), wherein the granules obtained in step c) are exposed at a temperature of 400° C. to 1100° C., to an atmosphere which comprises one or more reactive compounds selected from the group consisting of: chlorine; hydrochloric acid; sulphur halides; sulphur oxide halides; hydrogen; and mixtures thereof.

17. The process of claim 11, wherein step a) is performed by means of two compacting rollers and the specific pressure applied between the two compacting rollers is more than 12 kN/cm.

18. The process of claim 13, wherein the mesh size of the sieve used in step b) is 1000 μm-1500 μm.

19. The process of claim 18, wherein the mesh size of the sieve used in step c) of the process is 400 μm-600 μm.

20. The process of claim 19, further comprising step e), wherein the granules obtained in step c) of the process are exposed at a temperature of 400° C. to 1100° C., to an atmosphere which comprises one or more reactive compounds selected from the group consisting of: chlorine; hydrochloric acid; sulphur halides; sulphur oxide halides; hydrogen; and mixtures thereof.

* * * * *

UNITED STATES PATENT AND TRADEMARK OFFICE
CERTIFICATE OF CORRECTION

PATENT NO. : 12,330,951 B2
APPLICATION NO. : 17/927040
DATED : June 17, 2025
INVENTOR(S) : Giesseler et al.

Page 1 of 1

It is certified that error appears in the above-identified patent and that said Letters Patent is hereby corrected as shown below:

In the Specification

In Column 3; Line 59: the text d50 should be d90;

In Column 4; Line 6: the text 100 am should be 100 µm;

In Column 4; Line 14: the text (d50- d10)/ d50 should be (d90- d10)/ d50;

In Column 5; Line 12: the text >4 µm should be >4 nm;

In Column 5; Line 19: the text <4 am should be <4 µm;

In Column 8; Line 33: the text (C2) should be (Cl2);

In Column 8; Line 34: the text SC4 should be SCl4;

In Column 9; Line 21: the text (d10, d50, d50) should be (d10, d50, d90).

Signed and Sealed this
Nineteenth Day of August, 2025

Coke Morgan Stewart
*Acting Director of the United States Patent and Trademark Office*